US008870835B2

(12) United States Patent
Baid

(10) Patent No.: US 8,870,835 B2
(45) Date of Patent: Oct. 28, 2014

(54) NEEDLE SAFETY DEVICE FOR MEDICAL DEVICES

(75) Inventor: Rishi Baid, New Delhi (IN)

(73) Assignee: Poly Medicure Limited, Faridabad (IN)

( * ) Notice: Subject to any disclaimer, the term of this patent is extended or adjusted under 35 U.S.C. 154(b) by 0 days.

(21) Appl. No.: 13/696,165

(22) PCT Filed: May 4, 2011

(86) PCT No.: PCT/IB2011/051972
§ 371 (c)(1),
(2), (4) Date: Nov. 5, 2012

(87) PCT Pub. No.: WO2011/138746
PCT Pub. Date: Nov. 10, 2011

(65) Prior Publication Data
US 2013/0060199 A1 Mar. 7, 2013

(30) Foreign Application Priority Data
May 5, 2010 (IN) .............. 1058/DEL/2010

(51) Int. Cl.
*A61M 25/00* (2006.01)
*A61M 25/06* (2006.01)
*A61M 5/32* (2006.01)
(52) U.S. Cl.
CPC ......... *A61M 25/0618* (2013.01); *A61M 5/3273* (2013.01)
USPC .............. 604/263; 604/198; 604/192

(58) Field of Classification Search
USPC .................. 604/110, 190, 192, 263
See application file for complete search history.

(56) References Cited

U.S. PATENT DOCUMENTS

| 5,053,017 A | * | 10/1991 | Chamuel | 604/192 |
| 6,652,486 B2 | * | 11/2003 | Bialecki et al. | 604/110 |
| 2008/0249478 A1 | * | 10/2008 | Ishikura et al. | 604/198 |
| 2008/0269693 A1 | | 10/2008 | Steube et al. | |

FOREIGN PATENT DOCUMENTS

| EP | 1449554 | 8/2004 |
| WO | WO2009116080 | 9/2009 |

OTHER PUBLICATIONS

International Search Report; International Application No. PCT/IB2011/051972; Date of Actual Completion of International Search: Sep. 16, 2011; Date of Mailing of International Search Report: Sep. 26, 2011.

* cited by examiner

*Primary Examiner* — Laura Bouchelle
(74) *Attorney, Agent, or Firm* — Pearne & Gordon LLP

(57) ABSTRACT

A needle safety device for a medical device, in particular for an IV catheter assembly, being movably arranged on the needle comprising: a first part made of a suitable plastic material; a second part preferably made of a strip of suitable metal sheet; and a ring surrounding the first part and the second part having elastic properties made of suitable elastomeric material.

20 Claims, 10 Drawing Sheets

NEEDLE SAFETY DEVICE FOR MEDICAL DEVICES

RELATED APPLICATION INFORMATION

This application claims priority from PCT Patent Application No. PCT/IB2011/051972 filed on May 4, 2011, and Indian provisional Patent Application No. 1058/DEL/2010 filed on May 5, 2010. The entire content of which is incorporated herein by this reference. The applicants claim the benefit of this provisional application.

FIELD OF THE INVENTION

The invention generally relates to medical devices in particular to intravenous catheter assembly and more particularly to needle safety devices for preventing accidental pricking of, for example, health care workers by the needle after use.

BACKGROUND OF THE INVENTION

Medical needles are designed and manufactured specifically to be extremely sharp and to puncture skin and flesh of a patient with only the slightest force so that the medications may be conveniently administered. Dangers of accidental needle pricking while attending a patient are also well known. Once a needle has been used, it becomes contaminated with the patient's blood and becomes a potential threat, especially for the health care workers, in the spread of infectious diseases. During surgery, handling of these sharp instruments can lead to accidental sticks or puncture wounds exposing the healthcare worker to the infections such as AIDS and hepatitis. Being aware of risks of accidental pricks, health care workers take considerable precautions to avoid any inadvertent pricking by medical needles while attending a patient.

The chances of needle stick are increased during an emergency with several aspects require to be handled. Likewise, during disposal, an exposed needle point may be and usually is a threat to the medical waste handler.

A needle safety device of this kind is generally known and operative as a guard for the tip of a needle of the medical device. However, in some instances they are not entirely automatic requiring some extra effort like push or turn to initiate their operation during use. Such non-automatic needle guards have their obvious flaws such as manual operation of fixing the needle guard, the needle guard existing as a separate piece, difficulty in pushing the guard over the needle tip, loss of time, obvious danger of accidental prick etc.

The existing needle tip guards being the improvements over manually operated needle tip guards also suffer from certain flaws. In the arrangements of automatic needle guards, it has been found that after the needle guard is deployed and the needle with safety device is removed, there is a possibility that the needle guard may slip off/out of the crimp and/or from the hole/slot provided generally proximal to the needle tip. The slipping out may happen, if the needle guard is pulled from the tip or accidentally get pulled. The consequences of an exposed needle tip have already been discussed above.

Therefore, to help prevent health care workers from becoming infected by diseases while attending a patient from an accidental needle prick, there exists a constant need to have an improved needle safety device which without any extra effort automatically covers the tip of an intravenous needle after use and which cannot be pulled off the tip of the needle even under extreme accidental pressure.

SUMMARY OF THE INVENTION

A needle safety device is provided to prevent accidental pricking of health care workers after removal of the needle from the medical device.

It is an object of the present invention to provide an improved needle safety device for medical devices.

Another object of the present invention is to provide a very simple and inexpensive safety device for the tip of a medical device, for example intravenous catheter needle assembly which without affecting eases out its operation.

Yet another object of the present invention is to provide an improved needle safety device which operates entirely automatically and requires no additional action on the part of the health care workers beyond the normal process of insertion and withdrawal.

Yet another object of the present invention is to provide a needle safety device which has improved means and mechanism for automatically entrapping the needle tip and which becomes initiated when the needle penetrates the skin and automatically places the needle safety device over the tip of the needle when the needle is withdrawn.

Accordingly, the invention relates to a needle safety device for a medical device, in particular for an IV catheter assembly, being movably arranged on the needle comprising a first part made of a suitable plastic material; a second part preferably made of a strip of suitable metal sheet; and a ring surrounding the said first part and said second part having elastic properties made of suitable elastomeric material.

The invention also relates to an IV catheter assembly, comprising a catheter tube; a needle housing; a catheter housing having a proximal section and a distal section, wherein the distal section is joined to the catheter tube and the proximal section defines an enclosure to retain therein the said needle safety device prior to use; a needle having needle shaft with a proximal section and a distal section, wherein the distal section defines a needle tip and the proximal section is attached to the said needle housing; a said needle safety device movably arranged on the said needle in between the said catheter housing and said needle housing, wherein the said needle extends through the said needle device, wherein the top section forming the second arm of the second part of the said needle safety device deflectably rests on the said needle, and wherein the said needle safety device is removable from the said enclosure in the said catheter housing once the needle tip is received in the said needle safety device upon withdrawal of the needle from the said catheter tube.

BRIEF DESCRIPTION OF THE DRAWINGS

Preferred embodiments of the invention are described in the following description with reference to the appended drawings and wherein.

DETAILED DESCRIPTION OF THE INVENTION

As used herein, the term "proximal" refers to a location on the IV catheter assembly 10 with a needle safety device 12 of this invention closest to the clinician using the assembly 10 and farthest from the patient in connection with whom the assembly 10 is used in its normal operation. Conversely, the term "distal" refers to a location on the IV catheter assembly 10 with the needle safety device 12 of this invention farthest from the clinician using the assembly 10 and closest to the patient in connection with whom the assembly 10 is used in its normal operation.

The term "axial direction" refers to the direction indicated by 'A'.

Figure 1:
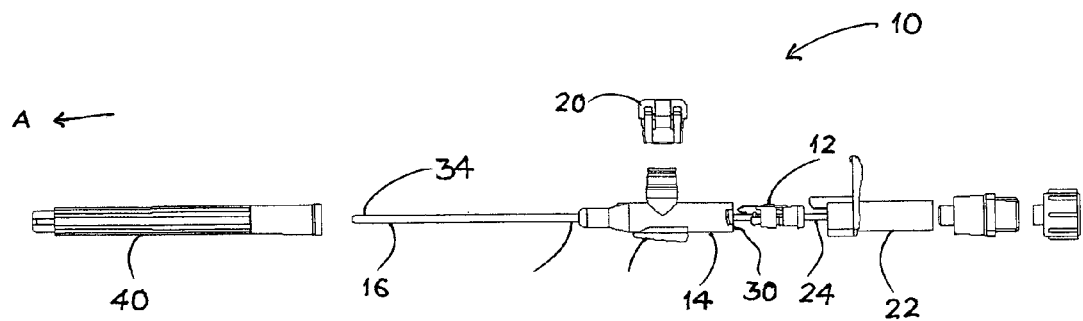
FIGS. 1 (*a*) and 1 (*b*) illustrate an exploded view of the IV catheter assembly with the needle safety device in accordance with the present invention.
Figure 1:
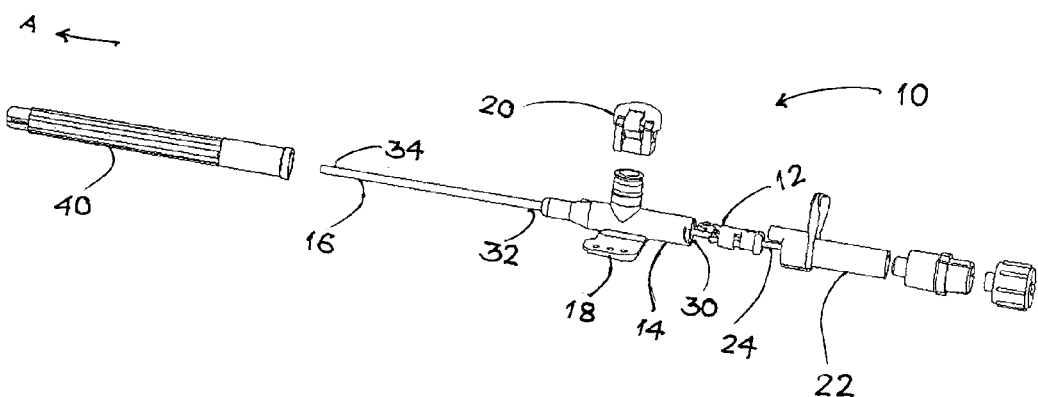

Referring now to appended drawings, FIGS. 1 (a) and 1(b) illustrate an exploded view of the IV catheter assembly 10 in accordance with the invention. The catheter assembly 10 includes catheter housing 14, a catheter tube 16, wings 18, a port 20, needle housing 22, a needle safety device 12 and a needle 24. The catheter housing 14 comprises a proximal section 26 and a distal section 28. The distal section 28 of the catheter housing 14 is joined to the catheter tube 16 and the proximal section 26 defines an enclosure 30 to retain the said needle safety device 12 therein prior to use.

Figure 2:
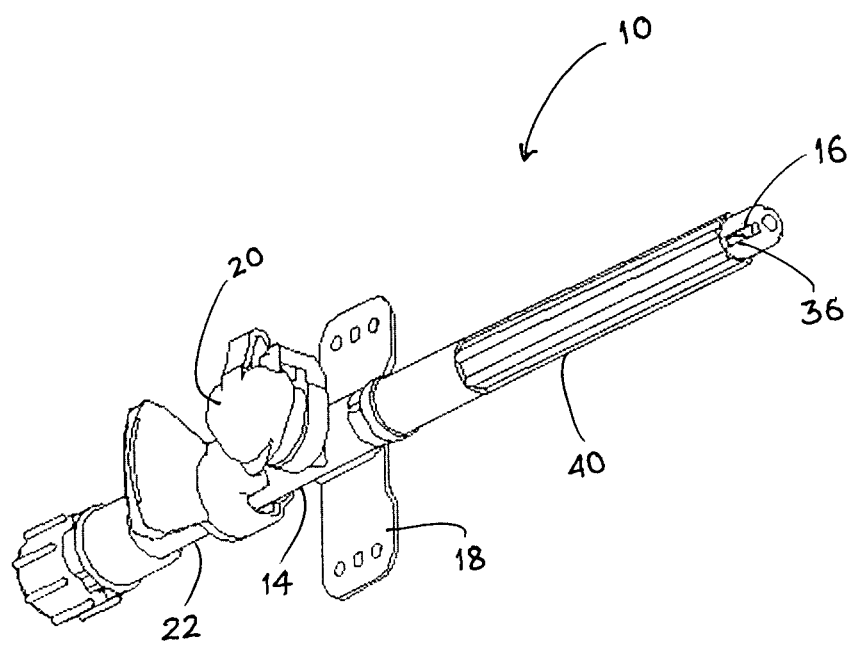
FIG. 2 illustrates a perspective view of the IV catheter assembly in its assembled position in accordance with the present invention.

Prior to use of the catheter assembly 10 as shown in FIG. 2, the needle housing 22 is connected to the catheter housing 14 and the needle tip 36 protrudes beyond the distal end region 34 of the catheter tube 16. The catheter tube comprises a proximal end region 32 and distal end region 34. The needle safety device 12 is movably arranged on the needle 24 between the catheter housing 14 and needle housing 22. As shown in FIGS. 1 (a) and 1 (b), the needle 24 is received in the catheter housing 14 and catheter tube 16, such that the needle shaft 38 extends through the length of the catheter tube 16. Thus, the needle 24 passes completely through the needle safety device 12 prior to use. Further, a protective cap 40 is mounted on the catheter housing 14 prior to use of the catheter assembly 10 in order to prevent accidental pricking by the protruding needle tip 36. The protective cap 40 covers the length of the catheter tube 16 and also the needle tip 36 protruding therefrom.

Figure 3:
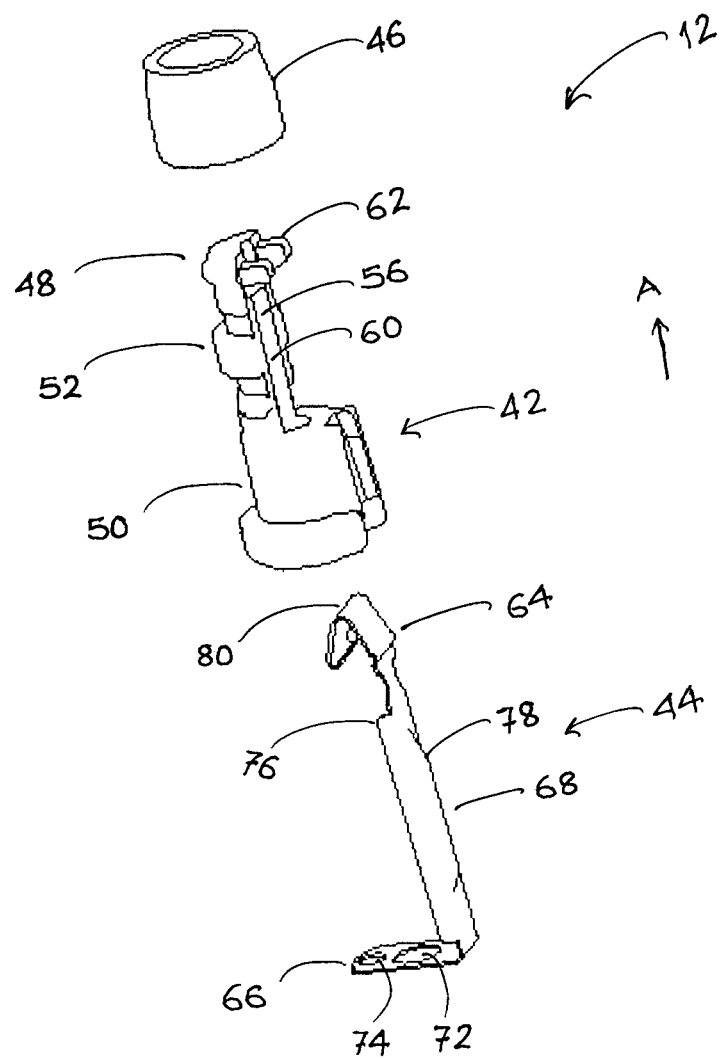
FIGS. 3 (*a*) and 3 (*b*) illustrate an exploded view of the needle safety device in accordance with the present invention.
Figure 3:
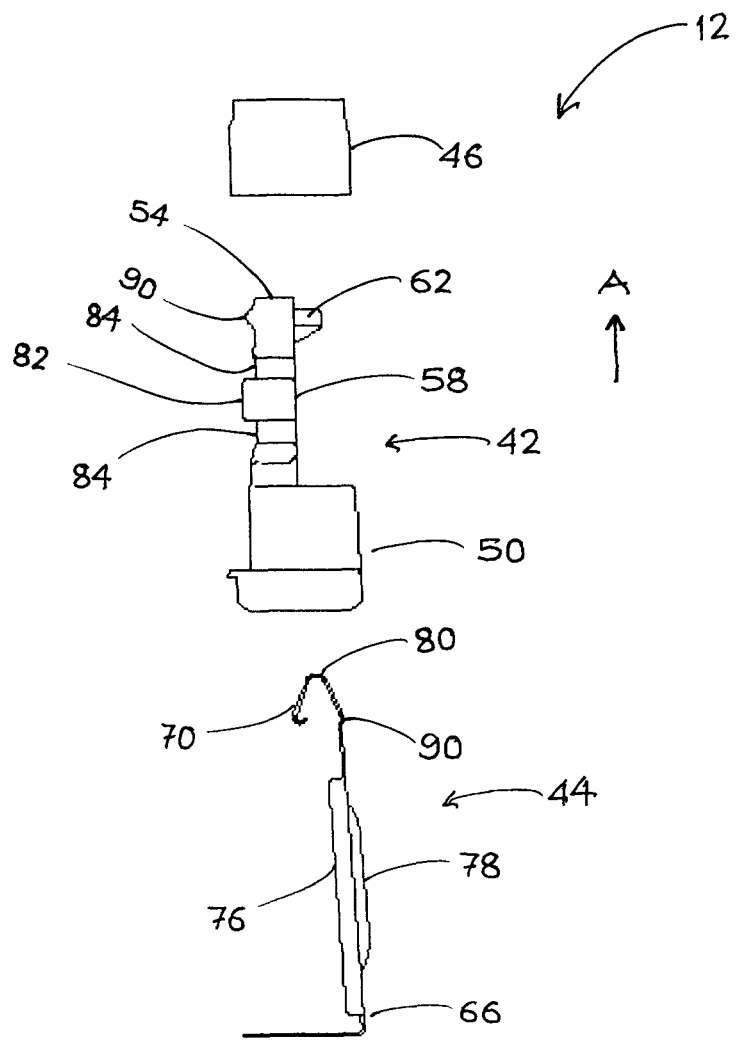
Figure 4:
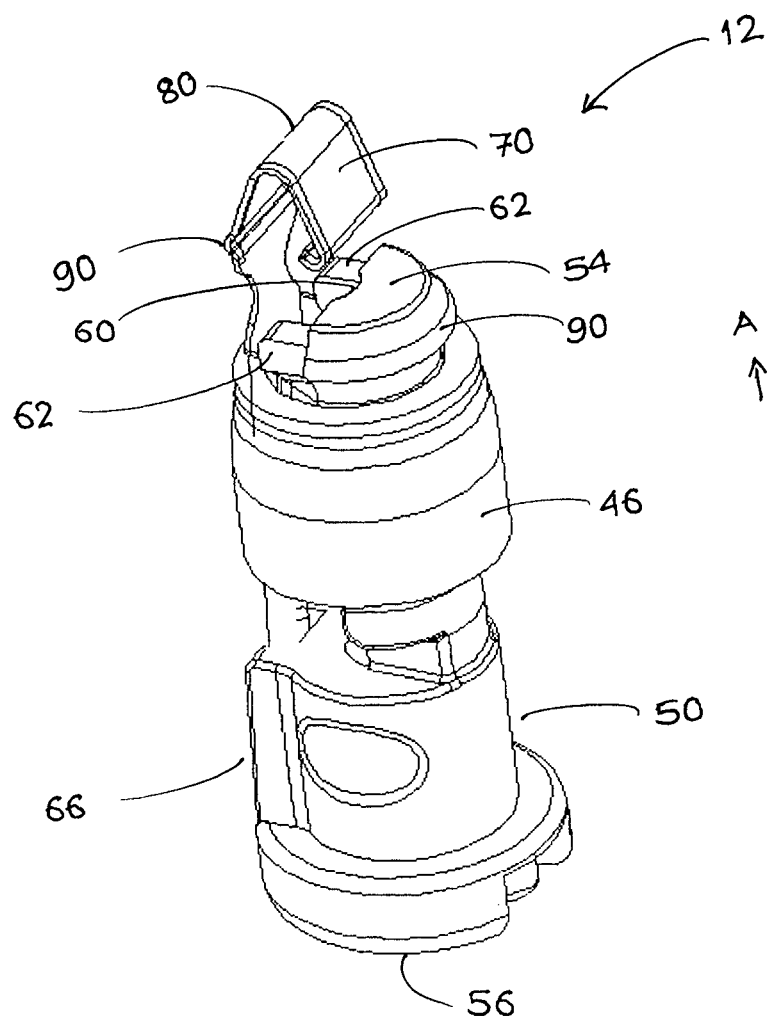
FIG. 4 illustrates a perspective view of the needle safety device in its assembled position in accordance with the present invention.

As illustrated in FIGS. 3 (a) and 3 (b), the needle safety device 12 comprises a first part 42, a second part 44 and a ring 46 surrounding the said first part 42 and said second part 44 having elastic properties. As illustrated further in FIG. 4. in its assembled form of the needle safety device 12, each of the first part 42, second part 44 and the ring 46 is secured together.

The first part 42 is made from a suitable plastic material and comprises a top section 48 forming a first arm 54, a base section 50 and a section in between the top 48 and base section 50 herein after middle section 52. The term 'middle section' 52 has been used for the purpose of illustration only and does not intend to divide the first part 42 by means of any equidistance arrangement or division. The base section 50 is substantially cylindrical in shape and has a bore 56 extending entirely through the middle section 52 in the axial direction towards the top section 48 to receive the needle 24. The top section 48 is substantially semi-cylindrical in shape and extends from the base section 50 entirely through the middle section 52 in the axial direction.

The top section 48 of the first part 42 at its inner wall 58 is provided with a groove 60 which extends in the axial direction towards the base section 50 along its entire length. The groove 60 has a substantially semi-circular shape as opposed to the generally circular-shape of the bore 56 provided in the base section 50 being adapted to the main outer profile of the needle 24.

The top section 48 comprises the formation of two projections 62 facing the top section 64 of the second part 44 ensuring the outer profile of the needle 24 to movably rest in the groove 60 formed in the inner wall 58 in a stable manner. The said projections 62 surround partially the needle 24 semi-circularly when the needle 24 passes through the bore 56 provided in the base section 50 of the first part 42 running there through in the axial direction towards the top sections 48, 64 of the said first part 42 and said second part 44.

The second part 44 comprises a top section 64 forming a second arm 70 having deflectable properties, a base section 66 and a section in between the top 64 and base 66 section herein after middle section 68. The term 'middle section' 68 herein has been used for illustration purpose only and does not intend to divide the second part 44 by means of any equidistance arrangement or division. The base section 66 of the second part 44 is adapted to engage with the base section of 50 the first part 42. The base section 66 of the second part 44 extends generally perpendicular to the middle section 68 of the second part 44. The base section 66 is provided with a generally circular hole 72 to receive the needle 24 in confirmation with the bore 56 provided in the base section 50 of the first part 42.

In addition to the hole 72, the base section 66 of the second part 44 is provided with an opening 74 to receive the pin (not shown here) formed in the base section 50 of the first part 42 when the second part 44 is mounted on the first part 42. While assembling, the second part 44 is brought into its correct position relative to the first part 42. The pin extending through the opening 74 of the second part 44 is deformed by heat and/or pressure in order to increase the diameter of the pin. By making the diameter of the pin larger than the diameter of the opening 74, the second part 44 is safely attached to the first part 42. The second part 44 is, thus, secured to the first part 42 by means of a heat sealing connection. Alternatively, the second part 44 could be secured to the first part 42 by means of welding or gluing or any other suitable type or means of connection.

The middle section 68 of the second part 44 comprises two elongate wings 76 that extend on either side of the middle section 68 part and are bent inwards, i.e. towards the middle section 52 of the first part 42 when secured therewith by an angle of about 90°. In a relaxed state, when the second part 44 is mounted on the first part 42, it can be seen in FIGS. 5 (a) and 5 (b) that the middle section 68 of the second part 44 does not exactly extend in the axial direction but is inclined slightly inwards towards the middle section 52 of the first part 42. Further, the middle section 68 of the second part 44 is provided with a bulge 78 extending outwardly from the said elongate wings 76.

The top section 64 of the second part 44 has a generally V-like shape with the peak 80 of the V pointing in the axial direction. The distal end of the V-like shape is bent inwards.

The free deflectable leg of the V-like shape of the top section 64 extends generally towards the top section 48 of the first part 42 when mounted thereon. Further, the V-like shape defines a space which covers and/or stops the distal end of the needle tip 36, once the needle tip 36 is received in the needle safety device 12. The disclosure herein is not intended to restrict the shape of the top section 64 part of the second part 44 only to the formation of V like shape, the shape thereof encompasses suitable other shapes, for example, a rectangular box like shape formation.

The second part 44 is formed as a single piece structure from a strip of suitable metal sheet having spring-like properties, such as steel or the like. Alternatively, the disclosure herein encompasses the scope of the second part 44 of the needle safety device 12 to be formed from a suitable plastic material having suitable spring-like properties.

The ring 46 having elastic properties surrounds the middle section 52 part of the first part 42 as well as the middle section 68 part of the second part 44. When surrounding the first 42 and second part 44, the ring 46 forces the second part 44 to be inclined slightly inwards towards the first part 42. As shown in FIG. 3 (b), the middle section 52 of the first part 42 of the needle safety device 12 at its outer surface is provided with a generally semi-circular projection(s) 82 along with depression(s) 84 running substantially parallel to the said projection 82. Likewise, the middle section 68 of the second part 44 of the needle safety device 12 is provided with a bulge 78 extending outwardly in an opposite direction to the elongate wings 76 provided therein. The said projection 82 and bulge 78 prevents the ring 46 from axially sliding off facilitating thereby a firm surrounding of the first 42 and second 44 part of the needle safety device 12 by the said ring 46.

The ring 46 is made from a suitable material such as suitable elastomeric material having elastic properties, for example, rubber or synthetic rubber. The elastic properties of the ring 46 ensure the tension facilitating further the deflection of first and second arm 70 of the first and second part 44 respectively of the needle safety device 12. Further, the substantially circular shape of the ring 46 is configured so that the deflectable top section 64 forming the second arm 70 of the second part 44 is deflected against a restoring force of the ring 46 when the needle 24 extends all the way through the needle safety device 12 between the first 54 and second arm 70.

Figure 6:
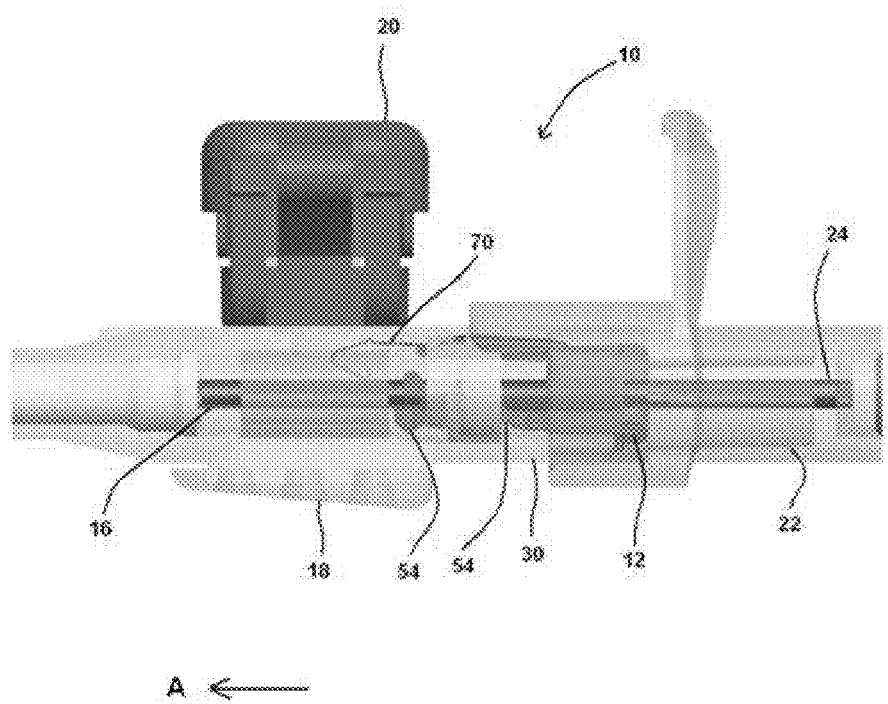
FIG. 6 (a) illustrates a see-through side view of the enlarged IV catheter assembly with the needle safety device being retained in the enclosure of the catheter housing, 6 (b) and 6 (c) illustrate a side view of the IV catheter assembly with the needle safety device movably arranged on the needle in accordance with the present invention.
Figure 6:
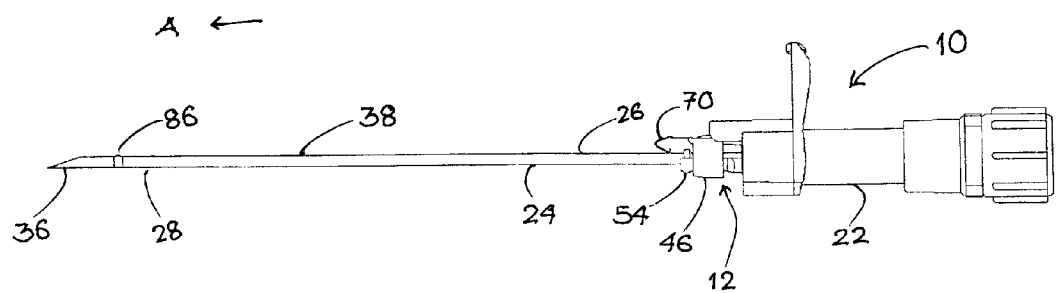
Figure 6:
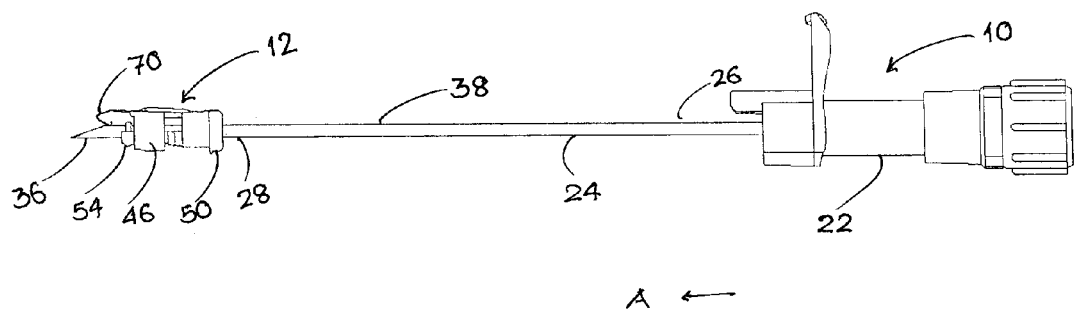
Figure 7:
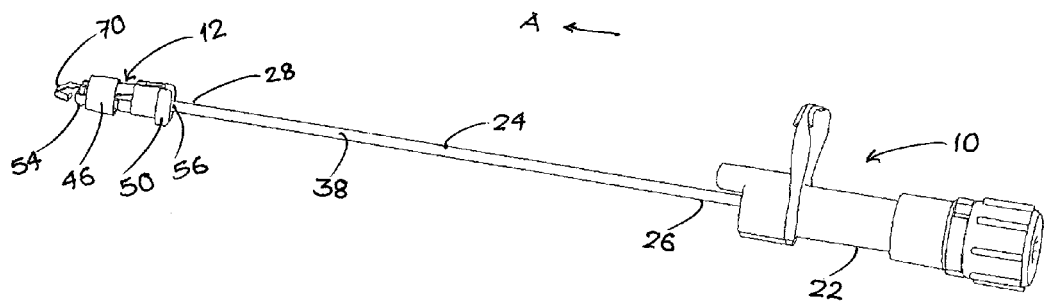
FIGS. 7 (a), 7 (b) and 7 (c) illustrate a perspective view, side view and a longitudinal sectional view respectively of the IV catheter assembly with the needle safety device securing the tip of the needle in accordance with the present invention.
Figure 7:
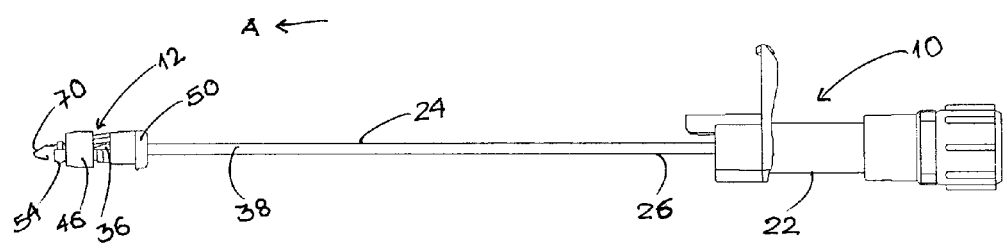
Figure 7:
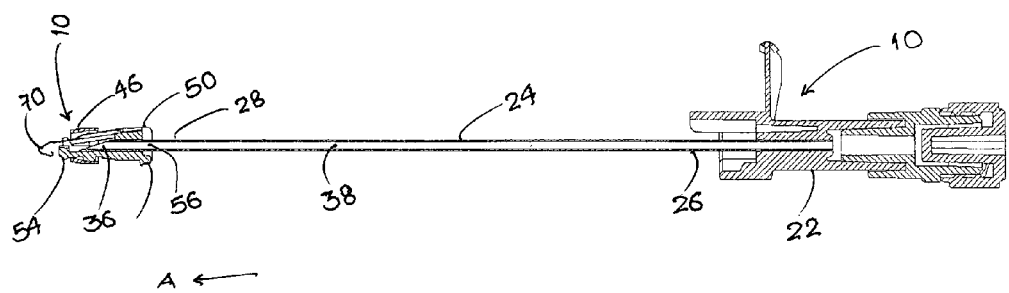

Further, the catheter assembly 10 comprises a needle 24, as shown in FIG. 6 (a) having a needle shaft 38 comprising a proximal section 26 and a distal section 28. The distal section 28 of the needle shaft 38 forms a needle tip 36 and the proximal section 26 of the needle shaft 38 is attached to the needle housing 22. Both, the distal section 28 and the proximal section 26 of the needle shaft 38 generally have the same outer profile. The needle shaft 38 is provided with an enlargement 86 in its outer profile close to the distal section 28 forming the needle tip 36. The enlargement 86 renders the outer diameter of the needle 24 greater than the diameter of the bore 56 provided in the needle safety device 12. The enlargement 86 prevents the needle safety device 12 from sliding off the needle 24 when the needle tip 36 is received between the first 54 and second 70 arms as illustrated in FIGS. 7 (a), 7 (b) and 7 (c) of the needle safety device 12. Moreover, the said needle tip 36 on being received between the said first 54 and said second arm 70 of the said needle safety device 12 allows the bore 56 in the base section 50 of the said first part 42 of the said needle safety device 12 to rest generally underneath the said enlargement 86 protecting the said needle tip 36. The enlargement 86 can be, for example, a bulge or a crimp. Alternatively, the enlargement 86 can be, for example, a hole or a slot.

As can be seen from FIGS. 1 (a) and 1 (b), prior to the use of the IV catheter assembly 10 the needle 24 extends through the catheter tube 16 and the needle safety device 12 is arranged movably in the catheter housing 14. In this situation, the top section 64 forming the second arm 70 of the second part 44 deflectably rests on the needle 24. The needle shaft 38 is securely positioned in the groove 60 provided in the inner wall 58 of the second part 44. The needle shaft 38 is, thus, supported in the groove 60. Due to which the top section 64 of the second part 44 forming the second arm 70 of the needle safety device 12 is deflected outwards, i.e. away from the needle 24 against a restoring force of the ring 46 having elastic properties. This deflected situation is called the deflected state of the needle safety device 12 and is illustrated further in FIGS. 6 (a), 6 (b) and 6 (c).

Figure 5:
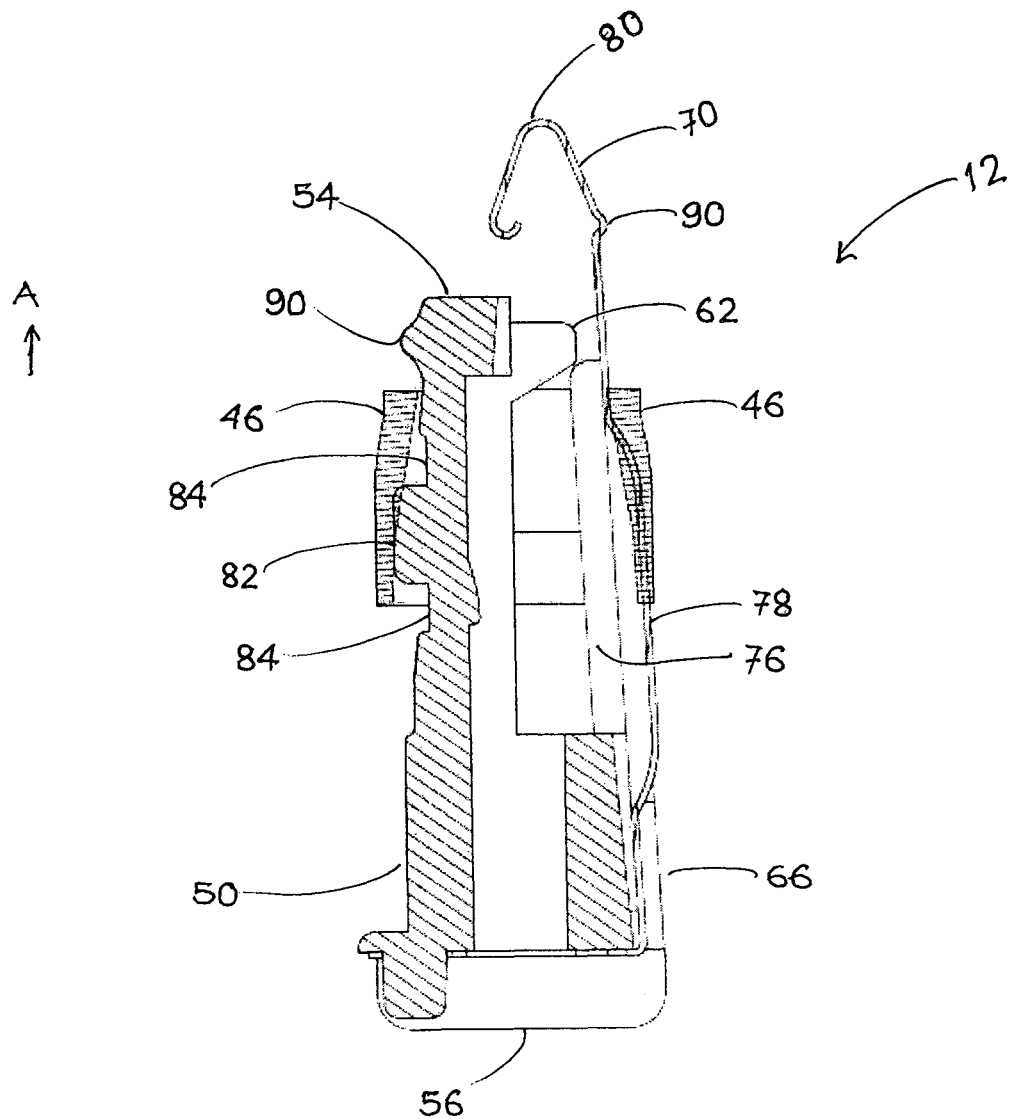
FIGS. 5 (a) and 5 (b) illustrate a longitudinal sectional view and side view respectively of the needle safety device in accordance with the present invention.
Figure 5:
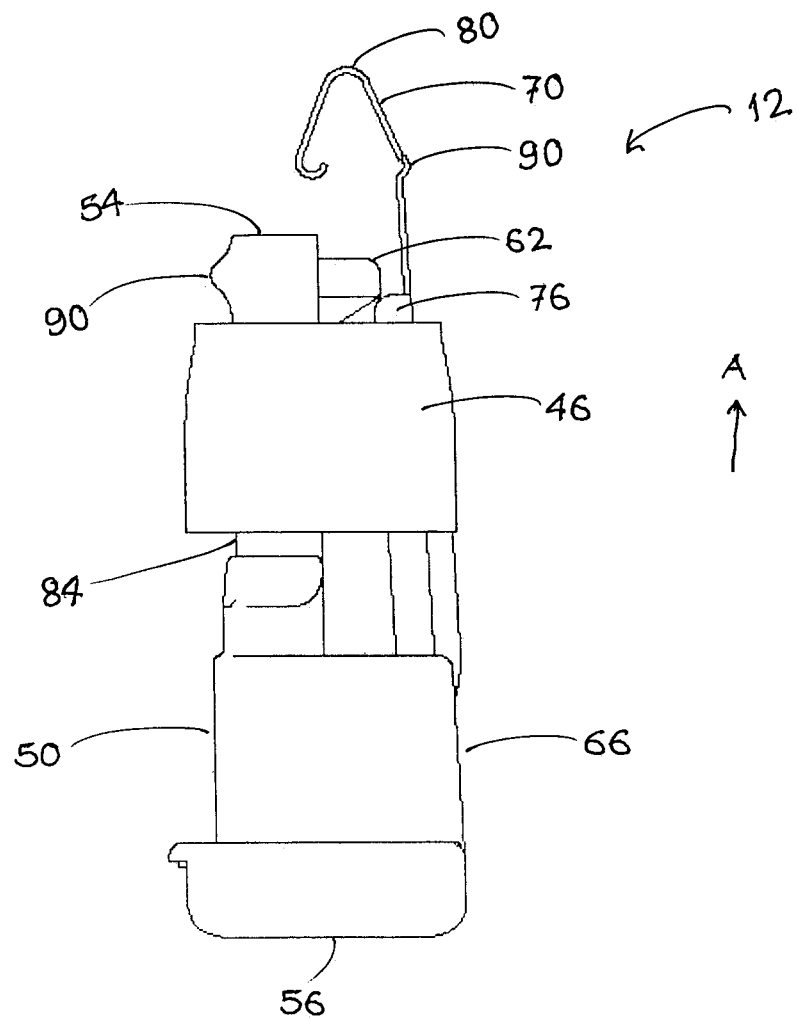

As opposed to the deflected state, when the needle 24 does not extends through the needle safety device 12 as shown in FIGS. 5 (a) and 5 (b), the deflectable top section 64 forming the second arm 70 is drawn inwardly towards the top section 48 of the first part 42 of the needle safety device 12 due to the elastic properties of the ring 46 surrounding the said first and second part 44. This situation is referred to as the reposited state of the needle safety device 12. As shown further in FIGS. 7 (a), 7 (b) and 7 (c), when the second arm 70 passes over the length of the needle shaft 38, and when the said second arm 70 does not deflectably rests on the needle 24, the said second arm 70 is likewise drawn inwardly towards the top section 48 forming the first arm 54 of the first part 42 of the needle safety device 12 due to the elastic properties of the ring 46 surrounding the said second and first part 42. This situation when the second arm 70 no longer deflectably rests on the needle 24 causes the said second arm 70 to reposit itself due to the restoring force being aided through the use of ring 46 having elastic properties.

As shown in FIG. 1 (b), when the needle 24 is being withdrawn from the catheter tube 16 of the catheter assembly 10 the needle 24 moves relative [FIG. 6 (b)] to the needle safety device 12 until the needle tip 36 is received in the said needle safety device 12. Once the needle tip 36 is received in the needle safety device 12, as shown in FIG. 7 (b), the enlargement 86 [FIG. 6 (a)] of the needle shaft 38 engages with the base section 50, 66 of the needle safety device 12 such that the safety device 12 can be pulled out of the catheter housing 14 together with the needle 24. In such a situation, the engagement between the enlargement 86 and the base section 50, 66 of the needle safety device 12 prevents the needle tip 36 from being removed from the needle safety device 12. Thus, as shown in FIGS. 7 (a), 7 (b) and 7 (c) the needle tip 36 is securely entrapped being safely surrounded by the needle safety device 12.

In use, while the needle 24 is being withdrawn from the catheter tube 16, the needle safety device 12 is retained in enclosure 30 of the catheter housing 14. In order to maintain the retainment of the needle safety device 12 in the enclosure 30 of the catheter housing 14, both the top section 48 part of the first part 42 forming the first arm 54 and the top section 64 part of the second part 44 forming the second arm 70 respectively are provided with shoulders 90 (FIGS. 1 (a) and 1 (b)]. The said shoulders 90 engage with one or more projections or protrusions or recesses or depressions or combinations thereof (not shown) provided in the catheter housing 14. The said projections or protrusions may form annular ring(s) extending along the entire inner periphery of the enclosure 30 of the catheter housing 14 or they may form one or more ring segments extending along only a respective part of the said inner periphery of the enclosure 30 of the catheter housing 14. Likewise, the said recesses or depressions may form annular groove(s) extending along the entire inner periphery of the catheter housing 14 or they may form one or more groove segments extending along only a respective part of the inner periphery of the catheter housing 14.

As mentioned above, in the reposited state the realignment of the second arm 70 causes the shoulders 90 to disengage from the said one or more projections or protrusions or recesses or depressions or combinations thereof allowing the needle safety device 12 to be withdrawn completely from the enclosure 30 provided in the catheter housing 14 with the needle tip 36 being entrapped safely by the needle safety device 12. Moreover, the said engagement means prevent the needle safety device 12 from being accidentally withdrawn from the catheter housing 14 before the needle tip 36 has been received between the said first 54 and second 70 arms of the needle safety device 12.

Due to its simple design the needle safety device 12 and, thus, the entire IV catheter assembly 10 can be manufactured at low cost. Even if an excessive external force is applied to the needle 24 and/or the needle safety device 12, the enlargement 86 provided on the needle shaft 38 proximal to the needle tip 36 being in engaged arrangement with the base section 50, 66 of the needle safety device 12 prevents the needle safety device 12 to be pulled off the needle shaft 38.

Although, the invention has been described with reference to certain specific embodiments and examples, it would be appreciated by those skilled in the art that the invention may be embodied in many forms without departing from the broader spirit and scope of the invention as set forth in the invention. Thus, variations of preferred embodiments as disclosed may become apparent to those of ordinary skill in the art upon reading the foregoing description.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. The specification and drawings, therefore, are to be regarded in an illustrative rather than a restrictive manner without departing from the spirit and scope of the invention, the invention resides in the claims hereinafter appended.

LIST OF REFERENCE NUMERALS

10 IV catheter assembly
12 needle safety device
14 catheter housing
16 catheter tube
18 wings
20 port
22 needle housing
24 needle
26 proximal section
28 distal section
30 enclosure
32 proximal end region
34 distal end region
36 needle tip
38 needle shaft
40 protective cap
42 first part
44 second part
46 ring
48 top section (first part)
50 base section (first part)
52 middle section (first part)
54 first arm
56 bore
58 inner wall
60 groove
62 projections
64 top section (second part)
66 base section (second part)
68 middle section (second part)
70 second arm
72 hole
74 opening
76 elongate wings
78 bulge
80 peak
82 semicircular projection
84 depression
86 enlargement
90 shoulders

The invention claimed is:

1. A needle safety device for a medical device being movably arranged on a needle comprising:
   a first part made of a suitable plastic material, said first part comprising a base section, a middle section, and a top section with a substantially semi-circular groove in its inner wall forming a first arm;
   a second part made of a strip of suitable metal sheet, said second part comprising: a base section being adapted to engage with the base section of said first part, a middle section, and a top section forming a deflectable second arm; and
   a ring surrounding said first part and said second part having elastic properties made of suitable elastomeric material, wherein
   said top section of said first part comprises the formation of two projections facing the top section of said second part ensuring the outer profile of the needle to movably rest in said groove; and both said first part forming the first arm and second part forming the second arm are provided with shoulders in their top section parts facilitating the retainment of the needle safety device in a catheter housing.

2. The needle safety device according to claim 1, wherein said base section is substantially cylindrical in shape comprising a through bore with a profile adapted to the principal outer profile of a needle shaft extending entirely through said middle section in the axial direction towards said top section to receive the needle.

3. The needle safety device according to claim 1, wherein said top section is substantially semi-cylindrical in shape and extends from the base section entirely through the middle section in the axial direction.

4. The needle safety device according to claim 3, wherein said substantially semi-circular groove in the inner wall of the said top section extends in an axial direction towards said base section along its entire length.

5. The needle safety device according to claim 1, wherein said base section of the second part extends generally perpendicular to said top section of said second part.

6. The needle safety device according to claim 5, wherein said base section of the second part is provided with a generally circular hole to receive the needle in confirmation with a bore provided in the base section of the first part.

7. The needle safety device according to claim 6, wherein said base section is provided with an opening to receive a pin formed in the base section of the first part when said second part is mounted on said first part.

8. The needle safety device according to claim 1, wherein said middle section of the second part comprises two elongate wings being bent inwards therefrom towards the middle section of said first part by an angle of about 90° being in a direction opposite to a bulge provided in said middle section of said second part.

9. The needle safety device according to claim 1, wherein said top section of the second part has a generally V-like shape with the peak of the V pointing in the axial direction defining a space which covers and/or stops the distal end of the needle tip.

10. The needle safety device according to claim 1, wherein said ring surrounds said first part and said second part covering generally the middle section parts of said first part and said second part.

11. The needle safety device according to claim 10, wherein said ring is configured so that the top section forming the second arm of said second part having deflectable properties is deflected outwardly against a restoring force of said ring when the needle extends all the way through the needle safety device such that said second arm rests deflectably on the needle shaft of the needle.

12. An IV catheter assembly, comprising:
a catheter tube;
a needle housing;
a catheter housing having a proximal section and a distal section wherein said distal section is joined to the catheter tube and the proximal section defines an enclosure to retain therein a needle safety device prior to use, said needle safety device being movably arranged on a needle and comprising:
a first part made of a suitable plastic material;
a second part made of a strip of suitable metal sheet; and
a ring surrounding said first part and said second part having elastic properties made of suitable elastomeric material;
said needle having a needle shaft with a proximal section and a distal section, wherein said distal section defines a needle tip and the proximal section is attached to said needle housing;
said needle safety device being movably arranged on said needle in between said catheter housing and said needle housing, wherein said needle extends through said needle device, wherein the top section forms a second arm of the second part of said needle safety device deflectably resting on said needle, and wherein said needle safety device is removable from said enclosure in said catheter housing once the needle tip is received in said needle safety device upon withdrawal of the needle from said catheter tube.

13. The IV catheter assembly according to claim 12, wherein one or more projections or protrusions or recesses or depressions or combinations thereof are provided in said enclosure of said catheter housing to facilitate retainment of said needle device.

14. The IV catheter assembly according to claim 12, wherein said needle shaft has an enlargement near the distal section of said needle rendering the outer diameter of said needle shaft generally greater than the diameter of a bore provided in said needle safety device.

15. The IV catheter assembly according to claim 12, wherein said needle tip on being received between a first arm and said second arm of said needle safety device allows a bore in the base section of said first part of said needle safety device to rest generally underneath an enlargement protecting said needle tip.

16. The IV catheter assembly according to claim 14, wherein said needle tip on being received between said first and said second arm of said needle safety device allows the bore in the base section of said first part of said needle safety device to rest generally underneath said enlargement protecting said needle tip.

17. An IV catheter assembly comprising the needle safety device of claim 1, said catheter assembly further comprising:
a catheter tube;
a needle housing;
a catheter housing having a proximal section and a distal section wherein said distal section is joined to the catheter tube and the proximal section defines an enclosure to retain therein the needle safety device prior to use;
a needle having needle shaft with a proximal section and a distal section, wherein said distal section defines a needle tip and the proximal section is attached to said needle housing;
a said needle safety device movably arranged on said needle in between said catheter housing and said needle housing, wherein said needle extends through said needle device, wherein the top section forming the second arm of the second part of said needle safety device deflectably rests on said needle, and wherein said needle safety device is removable from said enclosure in said catheter housing once the needle tip is received in said needle safety device upon withdrawal of the needle from said catheter tube.

18. An IV catheter assembly, comprising the needle safety device of claim 4, said catheter assembly further comprising:
a catheter tube;
a needle housing;
a catheter housing having a proximal section and a distal section wherein said distal section is joined to the catheter tube and the proximal section defines an enclosure to retain therein the needle safety device prior to use;
a needle having needle shaft with a proximal section and a distal section, wherein said distal section defines a needle tip and the proximal section is attached to said needle housing;
a said needle safety device movably arranged on said needle in between said catheter housing and said needle housing, wherein said needle extends through said needle device, wherein the top section forming the second arm of the second part of said needle safety device deflectably rests on said needle, and wherein said needle safety device is removable from said enclosure in said catheter housing once the needle tip is received in said needle safety device upon withdrawal of the needle from said catheter tube.

19. An IV catheter assembly, comprising the needle safety device of claim 7, said catheter assembly further comprising:
a catheter tube;
a needle housing;
a catheter housing having a proximal section and a distal section wherein said distal section is joined to the catheter tube and the proximal section defines an enclosure to retain therein the needle safety device prior to use;
a needle having needle shaft with a proximal section and a distal section, wherein said distal section defines a needle tip and the proximal section is attached to said needle housing;
a said needle safety device movably arranged on said needle in between said catheter housing and said needle housing, wherein said needle extends through said needle device, wherein the top section forming the second arm of the second part of said needle safety device deflectably rests on said needle, and wherein said needle safety device is removable from said enclosure in said catheter housing once the needle tip is received in said needle safety device upon withdrawal of the needle from said catheter tube.

20. A needle safety device for a medical device being movably arranged on a needle comprising:
   a first part made of a suitable plastic material;
   a second part made of a strip of suitable metal sheet; and
   a ring surrounding said first part and said second part having elastic properties made of suitable elastomeric material.

* * * * *